US008410096B2

(12) United States Patent
Park

(10) Patent No.: US 8,410,096 B2
(45) Date of Patent: Apr. 2, 2013

(54) ANTITUMOR AGENT, KIT AND METHOD OF TREATING CANCER

(75) Inventor: Sung Hwa Park, Shizuoka (JP)

(73) Assignees: Shizuoka Prefecture, Shizuoka-shi, Shizuoka (JP); Taiho Pharmaceutical Co., Ltd., Tokyo (JP)

( * ) Notice: Subject to any disclaimer, the term of this patent is extended or adjusted under 35 U.S.C. 154(b) by 284 days.

(21) Appl. No.: 12/944,797

(22) Filed: Nov. 12, 2010

(65) Prior Publication Data

US 2011/0136810 A1 Jun. 9, 2011

Related U.S. Application Data

(63) Continuation of application No. PCT/JP2009/058738, filed on May 11, 2009, and a continuation-in-part of application No. PCT/JP2008/065554, filed on Aug. 29, 2008.

(30) Foreign Application Priority Data

May 12, 2008 (JP) ................................. 2008-124504

(51) Int. Cl.
- A61K 31/53 (2006.01)
- A61K 31/505 (2006.01)
- A61K 31/4412 (2006.01)
- A61K 31/4985 (2006.01)
- A61K 31/282 (2006.01)

(52) U.S. Cl. ........ 514/241; 514/272; 514/274; 514/277; 514/492; 544/220; 544/242; 544/261; 556/136

(58) Field of Classification Search .................. None
See application file for complete search history.

(56) References Cited

U.S. PATENT DOCUMENTS

| 5,525,603 | A | 6/1996 | Shirasaka |
| 6,518,278 | B1 | 2/2003 | Oguro |
| 6,602,870 | B2 | 8/2003 | Chazard |
| 2004/0005365 | A1 | 1/2004 | Oguro |
| 2006/0116345 | A1 | 6/2006 | Uchida |
| 2008/0306073 | A1 | 12/2008 | Koizumi |

FOREIGN PATENT DOCUMENTS

| JP | 08-169825 A | 7/1996 |
| JP | 2557303 B2 | 9/1996 |
| JP | 2614164 B2 | 2/1997 |
| JP | 2002-205945 A | 7/2002 |
| WO | 92/04028 A1 | 3/1992 |
| WO | 92/21345 A1 | 12/1992 |
| WO | 2004/081012 A1 | 9/2004 |
| WO | 2005/120480 A1 | 12/2005 |

OTHER PUBLICATIONS

Schoffski, P., Anti-Cancer Drugs 2004, 15, 85-106.*
Mathe et al., Biomed. & Pharmacother. 1989, 43, 237-250.*
Raymond, et al. Annals of Oncology 1998, 9, 1053-1071.*
Yamada et al. British Journal of Cancer 2008, 98, 1034-1038.*
A. de Gramont et al., Leucovorin and Fluorouracil With or Without Oxaliplatin as First-Line Treatment in Advanced Colorect, Journal of Clinical Oncology, Aug. 2000, vol. 18, No. 16, pp. 2938-2947.
M. L. Rothenberg et al., Superiority of Oxaliplatin and Fluorouracil-Leucovorin Compared With Either Therapy Alone in Patients With Progressive Colorectal Cancer After Irinotecan and Fluorouracil-Leucovorin: Interim Results of a Phase III Trial, Journal of Clinical Oncology, Jun. 1, 2003, vol. 21, No. 11, pp. 2059-2069.
R. M. Goldberg et al., A Randomized Controlled Trial of Fluorouracil Plus Leucovorin, Irinotecan, and Oxaliplatin Combinations in Patients with Previously Untreated Metastatic Colorectal Cancer, Journal of Clinical Oncology, Jan. 1, 2004, vol. 22, No. 1, pp. 23-30.
O'Connell M. J., A phase III trial of 5-fluorouracil and leucovorin in the treatment of advanced colorectal cancer. A Mayo Clinic/North Central Cancer Treatment Group study., Cancer, Mar. 15, 1989, vol. 63 (6 Suppl), pp. 1026-1030.
Cassidy et al., "XELOX (Capecitabine Plus Oxaliplatin): Active First-Line therapy for Patients with Metastatic Colorectal Cancer", Journal of Clinical Oncology, vol. 22, 2084-2091, 2004.
Shizuoka Cancer Center, "Phase I/II Study of SOL for Untreated Metastatic Colorectal Cancer", Internet Website of ClinicalTrials. gov (http://clinicaltrials.gov/ct2/show/NCT005 24706), Sep. 4, 2007.

* cited by examiner

*Primary Examiner* — Sreeni Padmanabhan
*Assistant Examiner* — Irina Neagu
(74) *Attorney, Agent, or Firm* — Rothwell, Figg, Ernst & Manbeck, P.C.

(57) ABSTRACT

Disclosed are an antitumor preparation comprising a combination of (1) a combination drug of tegafur/gimeracil/oteracil potassium, (2) at least one ingredient selected from the group consisting of folinic acid and pharmacologically acceptable salts thereof, and (3) cis-oxalate(1R,2R-diaminocyclohexane)platinum(II); a kit comprising a combination of pharmaceutical compositions for treating cancer in a mammal, comprising: (a) a combination drug of tegafur/gimeracil/oteracil potassium in a therapeutically effective amount; (b) a composition containing at least one ingredient selected from the group consisting of folinic acid and pharmacologically acceptable salts thereof in an amount effective for enhancing antitumor effects, and (c) a composition containing cis-oxalate(1R,2R-diaminocyclohexane)platinum(II) in an amount effective for enhancing antitumor effects; and a method for treating cancer.

7 Claims, No Drawings

ANTITUMOR AGENT, KIT AND METHOD OF TREATING CANCER

CROSS REFERENCE TO RELATED APPLICATION

This application is a continuation of PCT/JP2009/058738 filed May. 11, 2009, and a continuation in part of PCT/JP2008/065554 filed Aug. 29, 2008 both of which claim the benefit of Japanese Patent Application No. 2008-124504 filed on May 12, 2008, the disclosures of which are incorporated herein in its entirety their reference.

TECHNICAL FIELD

The present invention relates to an antitumor preparation which uses a novel combination of antitumor agents, a kit for treating cancer, and a method for treating cancer intended to enhance antitumor effects.

BACKGROUND ART

Research and development of antitumor agents have been actively carried out, and a variety of potent antitumor agents are clinically used in the treatment of malignant tumors. Tegafur, for example, is a drug that is activated in vivo and gradually releases the active principle, 5-fluorouracil (hereinafter referred to as "5-FU"), thereby reducing the toxicity or side effects of 5-FU.

A combination drug of tegafur and uracil (trade name: UFT, tegafur:uracil (molar ratio)=1:4, manufactured by Taiho Pharmaceutical Co., Ltd.) is also known. Typically, 5-FU is rapidly metabolized in vivo and inactivated; however, this combination drug exhibits significantly enhanced antitumor effects compared to the use of tegafur alone, because uracil, which does not have antitumor activity by itself, inhibits the inactivation of 5-FU.

A three-drug combination of tegafur, gimeracil, and oteracil potassium (trade name: TS-1, tegafur:gimeracil:oteracil potassium (molar ratio)=1:0.4:1, manufactured by Taiho Pharmaceutical Co., Ltd.) is also known. This combination drug exhibits further enhanced antitumor effects because gimeracil has 5-FU decomposition inhibitory action about 200 times higher than that of uracil. Furthermore, this combination drug exhibits enhanced therapeutic effects, because oteracil potassium specifically inhibits a potential increase in gastrointestinal toxicity caused by the enhanced antitumor effects provided by tegafur and gimeracil (Patent Literature 1). UFT and TS-1 are thus contributing to the treatment of various malignant tumors.

However, there is still a need for drugs and therapeutic methods that provide further enhanced therapeutic effects so as to further prolong the survival of cancer patients. For this purpose, attempts (combination therapies) have been made to enhance therapeutic results by administering in combination a plurality of drugs having different mechanisms of expressing antitumor action and having different side effects. For example, it has been disclosed that the use of folinic acid or a salt thereof in combination with an antitumor agent containing a combination drug of tegafur and uracil, or a three-drug combination of tegafur, gimeracil, and oteracil potassium can significantly enhance the antitumor effects of the antitumor preparation without increasing toxicity, thereby contributing to enhancing therapeutic results (see, for example, Patent Literatures 2 to 6). For example, oxaliplatin, which exhibits low antitumor effects when used alone, is used with other pharmaceutical agents in combination therapies. Combination therapies using oxaliplatin together with 5-fluorouracil and calcium folinate (FOLFOX) are commonly practiced worldwide (see, for example, Non-Patent Literatures 1, 2, and 3). However, because of its complicated procedures, FOLFOX poses problems such as decreased QOL of patients due to the restraints that accompany continuous infusion and high medical costs. Therefore, the development of better combination therapies using oxaliplatin has been sought all over the world. One such example is a combination therapy using oxaliplatin together with capecitabine, which is an oral fluorinated pyrimidine-based anticancer agent (trade name: Xeroda). This combination therapy (XELOX) has been reported to provide antitumor effects substantially equal to FOLFOX (see Non-Patent Literature 4). Moreover, a new approach using oxaliplatin with TS-1 has been indicated as a therapeutic method that significantly potentiates the antitumor effects, and that exhibits high efficacy even compared to that resulting from the combined use of oxaliplatin and capecitabine (see Patent Literature 7). However, in order to prolong the survival of patients, there is still a need for the development of a pharmaceutical preparation and a therapeutic method that provide further enhanced therapeutic effects.

Citation List

Patent Literature
PTL 1: Japanese Patent Publication No. 2614164
PTL 2: Japanese Patent Publication No. 2557303
PTL 3: WO 2004/081012
PTL 4: Japanese Unexamined Patent Publication No. 8-169825
PTL 5: Japanese Unexamined Patent Publication No. 2002-205945
PTL 6: U.S. Pat. No. 6,602,870
PTL 7: WO 2005/120480

Non-patent Literature
NPTL 1: *Journal of Clinical Oncology*, Vol. 22, 22-30, 2004
NPTL 2: *Journal of Clinical Oncology*, Vol. 21, 2059-2069, 2003
NPTL 3: *Journal of Clinical Oncology*, Vol. 18, 2938-2947, 2000
NPTL 4: *Journal of Clinical Oncology*, Vol. 22, 2084-2091, 2004

SUMMARY OF INVENTION

Technical Problem

A principal object of the invention is to provide an antitumor preparation, a kit, and a method for treating cancer that exhibit excellent therapeutic effects through the combined use of a combination drug of tegafur/gimeracil/oteracil potassium and other pharmaceutical preparations.

Solution to Problem

In view of the above-mentioned current state of the art, the inventors studied a novel combination therapy that uses a three-drug combination of tegafur, gimeracil, and oteracil potassium together with other pharmaceutical agents, in order to develop a method for treating cancer that contributes to further prolonging the survival of patients. As a result, they found that the use of the three-drug combination with at least one ingredient selected from the group consisting of folinic acid and pharmacologically acceptable salts thereof (hereinafter referred to as LV), and a platinous complex, i.e., cis-oxalate(1R,2R-diaminocyclohexane)platinum(II) (generic name: oxaliplatin, trade names: Eloxatin and Elplat, hereinafter referred to as l-OHP), significantly enhances antitumor effects without aggravating side effects. The present inventors also ascertained that the inhibitory effect upon tumor growth attained by this novel combination therapy is superior to that of standard chemotherapies for colon cancer that have previously been used. The present invention has been accomplished based on these findings.

In summary, the invention provides an antitumor preparation, an antitumor preparation kit, a method for treating cancer, and the like, as itemized below.

Item 1.

An antitumor preparation comprising a combination of
(1) a combination drug of tegafur/gimeracil/oteracil potassium,
(2) at least one ingredient selected from the group consisting of folinic acid and pharmacologically acceptable salts thereof, and
(3) cis-oxalate(1R,2R-diaminocyclohexane)platinum(II).

Item 2.

The antitumor preparation according to Item 1, which is in a pharmaceutical form comprising a plurality of pharmaceutical agents, each containing one or a desired combination of the following active ingredients: (1) a combination drug of tegafur/gimeracil/oteracil potassium, (2) at least one ingredient selected from the group consisting of folinic acid and pharmacologically acceptable salts thereof, and (3) cis-oxalate(1R,2R-diaminocyclohexane)platinum(II); or which is in a pharmaceutical form comprising a single pharmaceutical agent containing all of the active ingredients.

Item 3.

The antitumor preparation according to Item 2, which is in a pharmaceutical form comprising (1) a combination drug of tegafur/gimeracil/oteracil potassium, (2) a pharmaceutical agent containing, as an active ingredient, at least one ingredient selected from the group consisting of folinic acid and pharmacologically acceptable salts thereof, and (3) a pharmaceutical agent containing cis-oxalate(1R,2R-diaminocyclohexane)platinum(II) as an active ingredient.

Item 4.

The antitumor preparation according to Item 1, which is in a pharmaceutical form comprising (1) a pharmaceutical agent containing, as active ingredients, tegafur, gimeracil, and oteracil potassium, and at least one ingredient selected from the group consisting of folinic acid and pharmacologically acceptable salts thereof, and (2) a pharmaceutical agent containing cis-oxalate(1R,2R-diaminocyclohexane)platinum(II) as an active ingredient.

Item 5.

The antitumor preparation according to any one of Items 1 to 4, wherein the combination drug of tegafur/gimeracil/oteracil potassium comprises tegafur, gimeracil, and oteracil potassium in a molar ratio of 1:0.4:1.

Item 6.

The antitumor preparation according to any one of Items 1 to 5, wherein the proportions of the active ingredients are such that, per mole of tegafur, the proportion of gimeracil is 0.1 to 5 mol; the proportion of oteracil potassium is 0.1 to 5 mol; the proportion of the at least one ingredient selected from the group consisting of folinic acid and pharmacologically acceptable salts thereof is 0.01 to 10 mol; and the proportion of cis-oxalate(1R,2R-diaminocyclohexane)platinum(II) is 0.1 to 5 mol.

Item 7.

The antitumor preparation according to Item 6, wherein the molar ratio of the active ingredients is such that tegafur/gimeracil/oteracil potassium/the at least one ingredient selected from the group consisting of folinic acid and pharmacologically acceptable salts thereof/cis-oxalate(1R,2R-diaminocyclohexane)platinum(II)=1:0.4:1:0.01 to 10:0.1 to 5.

Item 8.

The antitumor preparation according to any one of Items 1 to 7, wherein the combination drug of tegafur/gimeracil/oteracil potassium and the pharmaceutical agent containing, as an active ingredient, at least one ingredient selected from the group consisting of folinic acid and pharmacologically acceptable salts thereof are orally administered; and the pharmaceutical agent containing cis-oxalate(1R,2R-diaminocyclohexane)platinum(II) as an active ingredient is administered intravenously, intramuscularly, or subcutaneously.

Item 9.

The antitumor preparation according to any one of Items 1 to 5, wherein the antitumor preparation is administered such that the dose of tegafur of the combination drug of tegafur/gimeracil/oteracil potassium is 40 mg/m$^2$/bid, the dose of the at least one ingredient selected from the group consisting of folinic acid and pharmacologically acceptable salts thereof is 25 mg/body/bid, and the dose of cis-oxalate(1R,2R-diaminocyclohexane)platinum(II) is 85 mg/m$^2$.

Item 10.

The antitumor preparation according to any one of Items 1 to 5, wherein cis oxalate(1R,2R-diaminocyclohexane)platinum(II) is administered by intravenous drip infusion, and the combination drug of tegafur/gimeracil/oteracil potassium and the at least one ingredient selected from the group consisting of folinic acid and pharmacologically acceptable salts thereof are orally administered; and wherein the cis-oxalate (1R,2R-diaminocyclohexane)platinum(II) is administered at a dose of 85 mg/m$^2$ on day one, and the combination drug of tegafur/gimeracil/oteracil potassium and the at least one ingredient selected from the group consisting of folinic acid and pharmacologically acceptable salts thereof are administered at doses of 40 mg/m$^2$/bid (calculated as the amount of tegafur) and 25 mg/body/bid, respectively, from day one for one week.

Item 11.

The antitumor preparation according to any one of Items 1 to 10, wherein the antitumor preparation is a kit comprising:
(1) a combination drug of tegafur/gimeracil/oteracil potassium,
(2) a pharmaceutical agent containing at least one ingredient selected from the group consisting of folinic acid and pharmacologically acceptable salts thereof, and
(3) a pharmaceutical agent containing cis-oxalate(1R,2R-diaminocyclohexane)platinum(II).

Item 12.

A kit comprising a combination of pharmaceutical compositions for treating cancer in a mammal, comprising:
(a) an antitumor composition containing tegafur in a therapeutically effective amount, gimeracil in an amount effective for enhancing antitumor effects, and oteracil potassium in an amount effective for reducing side effects;
(b) a composition containing at least one ingredient selected from the group consisting of folinic acid and pharmacologically acceptable salts thereof in an amount effective for enhancing antitumor effects, and
(c) a composition containing cis-oxalate(1R,2R-diaminocyclohexane)platinum(II) in an amount effective for enhancing antitumor effects.

Item 13.

The kit according to Item 12, wherein cis-oxalate(1R,2R-diaminocyclohexane)platinum(II) is administered by intravenous drip infusion, and the combination drug of tegafur/gimeracil/oteracil potassium and the at least one ingredient selected from the group consisting of folinic acid and pharmacologically acceptable salts thereof are orally administered; and wherein the cis-oxalate(1R,2R-diaminocyclohexane)platinum(II) is administered at a dose of 85 mg/m$^2$ on day one, and the combination drug of tegafur/gimeracil/oteracil potassium and the at least one ingredient selected from the group consisting of folinic acid and pharmacologically acceptable salts thereof are administered at doses of 40 mg/m$^2$/bid (calculated as the amount of tegafur) and 25 mg/body/bid, respectively, from day one for one week.

Item 14.

A method for treating cancer comprising co-administering to a mammal (1) a combination drug of tegafur/gimeracil/oteracil potassium in a therapeutically effective amount, (2) at least one ingredient selected from the group consisting of folinic acid and pharmacologically acceptable salts thereof in an amount effective for enhancing antitumor effects, and (3) cis-oxalate(1R,2R-diaminocyclohexane)platinum(II) in an amount effective for enhancing antitumor effects.

Item 15.

The method for treating cancer according to Item 14, wherein the combination drug of tegafur/gimeracil/oteracil potassium comprises tegafur, gimeracil, and oteracil potassium in a molar ratio of 1:0.4:1.

Item 16.

The method for treating cancer according to Item 14 or 15, wherein the proportions of the active ingredients are such that, per mole of tegafur, the proportion of gimeracil is 0.1 to 5 mol, the proportion of oteracil potassium is 0.1 to 5 mol, the proportion of the at least one ingredient selected from the group consisting of folinic acid and pharmacologically acceptable salts thereof is 0.01 to 10 mol, and the proportion of cis-oxalate(1R,2R-diaminocyclohexane)platinum(II) is 0.1 to 5 mol.

Item 17.

The method for treating cancer according to Item 16, wherein the molar ratio of the active ingredients is such that tegafur/gimeracil/oteracil potassium/the at least one ingredient selected from the group consisting of folinic acid and pharmacologically acceptable salts thereof/cis-oxalate(1R,2R-diaminocyclohexane)platinum(II)=1:0.4:1:0.01 to 10:0.1 to 5.

Item 18.

Use of at least one ingredient selected from the group consisting of folinic acid and pharmacologically acceptable salts thereof, and cis-oxalate(1R,2R-diaminocyclohexane)platinum(II), for the manufacture of an antitumor preparation having enhanced antitumor effects, in the manufacture of an antitumor preparation containing a therapeutically effective amount of a combination drug of tegafur/gimeracil/oteracil potassium.

Item 19.

Use of at least one ingredient selected from the group consisting of folinic acid and pharmacologically acceptable salts thereof, and cis oxalate(1R,2R-diaminocyclohexane)platinum(II), for the manufacture of an antitumor-effect potentiator that enhances antitumor effects of an antitumor preparation containing a therapeutically effective amount of a combination drug of tegafur/gimeracil/oteracil potassium.

Item 20.

A composition for use in the treatment of cancer, comprising (1) a combination drug of tegafur/gimeracil/oteracil potassium in a therapeutically effective amount, (2) at least one ingredient selected from the group consisting of folinic acid and pharmacologically acceptable salts thereof in an amount effective for enhancing antitumor effects, and (3) cis-oxalate(1R,2R-diaminocyclohexane)platinum(II) in an amount effective for enhancing antitumor effects.

A feature of the antitumor preparation of the invention is that the preparation comprises a combination of a combination drug of tegafur/gimeracil/oteracil potassium, at least one ingredient selected from the group consisting of folinic acid and pharmacologically acceptable salts thereof, and cis-oxalate(1R,2R-diaminocyclohexane)platinum(II). Another feature of the antitumor preparation is that the preparation is in a pharmaceutical form comprising a plurality of pharmaceutical agents, each containing one or a desired combination of the active ingredients, or in a pharmaceutical form comprising a single pharmaceutical agent containing all of the active ingredients.

A feature of the kit of the invention is that the kit comprises a combination of pharmaceutical compositions for treating cancer in a mammal, comprising (a) a combination drug of tegafur/gimeracil/oteracil potassium, (b) a pharmaceutical agent containing at least one ingredient selected from the group consisting of folinic acid and pharmacologically acceptable salts, and (c) a pharmaceutical agent containing cis-oxalate(1R,2R-diaminocyclohexane)platinum(II).

A feature of the method for treating cancer of the invention is that the method comprises co-administering to a mammal a combination drug of tegafur/gimeracil/oteracil potassium in a therapeutically effective amount, at least one ingredient selected from the group consisting of folinic acid and pharmacologically acceptable salts thereof in an amount effective for enhancing antitumor effects, and cis-oxalate(1R,2R-diaminocyclohexane)platinum(II) in an amount effective for enhancing antitumor effects.

With respect to the composition for use in the treatment of cancer that comprises (1) a combination drug of tegafur/gimeracil/oteracil potassium in a therapeutically effective amount, (2) at least one ingredient selected from the group consisting of folinic acid and pharmacologically acceptable salts thereof in an amount effective for enhancing antitumor effects, and (3) cis-oxalate(1R,2R-diaminocyclohexane)platinum(II) in an amount effective for enhancing antitumor effects, the term "composition" as used herein indicates both concurrent use and successive use of the ingredients contained therein.

The term "active ingredient" or "active ingredients" as used herein means both ingredient(s) having antitumor activity and ingredient(s) that enhance antitumor effects.

Folinic acid used as an active ingredient is a known compound, and has conventionally been used mainly as an agent for reducing the toxicity of folic acid antagonists. Folinic acid has two optical isomers, i.e., the d- and l-isomers. In the invention, the d-isomer, l-isomer, and a mixture thereof can be used. In particular, the l-isomer, or a mixture of the d- and l-isomers is preferably used. One example of a pharmacologically acceptable salt of folinic acid is a calcium salt.

In the invention, the phrase "at least one ingredient selected from the group consisting of folinic acid and pharmacologically acceptable salts thereof" means at least one compound selected from the group consisting of folinic acid and pharmacologically acceptable salts thereof.

l-OHP used as an active ingredient is a complex containing platinum, and is a known compound. l-OHP acts to annihilate cancer cells by binding to the DNA of the cancer cells to thereby induce DNA dysfunction and DNA strand cleavage. l-OHP can be produced according to known methods, for example, the method disclosed in Japanese Examined Patent Publication No. 60-41077.

Tegafur (generic name, chemical name: 5-fluoro-1-(2-tetrahydrofuryl)-2,4-(1H, 3H)-pyrimidinedione, hereinafter sometimes referred to as FT), which is an active ingredient of the combination drug, is a known compound, and is a pharmaceutical agent that is activated in vivo and gradually releases 5-FU, which is the active principle of antitumor activity. Tegafur can be produced according to known methods, for example, the method disclosed in Japanese Examined Patent Publication No. 49-10510.

Gimeracil (generic name, chemical name: 2,4-dihydroxy-5-chloropyridine, hereinafter sometimes referred to as CDHP) is also a known compound, and can potentiate antitumor effects by inhibiting the in vivo metabolic inactivation of 5-FU.

Oteracil potassium (generic name, chemical name: monopotassium 1,2,3,4-tetrahydro-2,4-dioxo-1,3,5-triazine-6-carboxylate, hereinafter sometimes referred to as OXO) is also a known compound; it mostly remains in the gastrointestinal tract to inhibit the activation of 5-FU at that site, thereby preventing gastrointestinal tract disorders.

The phrase "a combination drug of tegafur/gimeracil/oteracil potassium" as used herein means a three-drug combination of tegafur, gimeracil, and oteracil potassium. Preferably, the combination drug contains, per mole of tegafur, about 0.1 to about 5 mol, and preferably about 0.2 to about 1.5 mol of gimeracil, and about 0.1 to about 5 mol, and preferably about 0.2 to about 2 mol of oteracil potassium. Most preferably the combination drug contains TS-1. The phrase "a combination drug of tegafur/gimeracil/oteracil potassium" also means both the form of a compound of these three ingredients, and the form of a pharmaceutical agent containing these three ingredients as active ingredients.

The phrase "a combination drug of tegafur/gimeracil/oteracil potassium in a therapeutically effective amount" as used herein means a three-drug combination containing tegafur in a therapeutically effective amount, gimeracil in an amount effective for enhancing antitumor effects, and oteracil potassium in an amount effective for reducing side effects. Preferably, the combination drug contains, per mole of tegafur, about 0.1 to about 5 mol, and preferably about 0.2 to about 1.5 mol of gimeracil; and about 0.1 to about 5 mol, and preferably about 0.2 to about 2 mol of oteracil potassium. Most preferably the combination drug contains TS-1.

In the antitumor agent containing the three active ingredients, i.e., tegafur, gimeracil, and oteracil potassium, the proportion of each ingredient may be within a range similar to that of a known combination drug described in, for example, Japanese Patent Publication No. 2614164. Typically, per mole of tegafur, gimeracil is used in a proportion of about 0.1 to about 5 mol, and preferably about 0.2 to about 1.5 mol, and oteracil potassium is used in a proportion of about 0.1 to about 5 mol, and preferably about 0.2 to about 2 mol. A particularly preferred proportion of the three ingredients is such that tegafur/gimeracil/oteracil potassium (molar ratio)=1:0.4:1 (hereinafter, the combination drug containing the three ingredients in this ratio is sometimes referred to as TS-1).

The antitumor agent containing the three active ingredients, i.e., tegafur, gimeracil, and oteracil potassium, is prepared into a pharmaceutical composition according to a general method, using suitable pharmaceutical carriers. Examples of usable carriers include those generally used for drugs, such as excipients, binders, disintegrators, lubricants, colorants, taste enhancers, flavor enhancers, and surfactants.

Unit dosage forms for administering the antitumor agent containing the three active ingredients, i.e., tegafur, gimeracil, and oteracil potassium, for the treatment of malignant tumors in mammals, including humans, are not particularly limited, and can be suitably selected according to the purpose of the treatment. Specific examples of such unit dosage forms include parenteral forms such as injections, suppositories, ophthalmic solutions, ointments, aerosols, and the like; and oral forms such as tablets, coated tablets, powders, granules, capsules, fluids, pills, suspensions, emulsions, and the like, with oral forms being preferred. These dosage forms can be produced according to methods generally known in the art.

A pharmaceutical agent containing, as an active ingredient, at least one ingredient selected from the group consisting of folinic acid and pharmacologically acceptable salts is prepared into a pharmaceutical composition according to a general method, using suitable pharmaceutical carriers. Examples of usable carriers include those generally used for drugs, such as excipients, binders, disintegrators, lubricants, colorants, taste enhancers, flavor enhancers, and surfactants. The pharmaceutical agent that has been prepared into a desired unit dosage form can be administered concurrently with, or separately from, the antitumor agent containing the three active ingredients, i.e., tegafur, gimeracil, and oteracil potassium, that has also been prepared into a desired unit dosage form. More specifically, the pharmaceutical agent of the invention containing at least one ingredient selected from the group consisting of folinic acid and pharmacologically acceptable salts can be administered at a desired time point, i.e., before, after, or concurrently with the administration of the antitumor agent containing the three active ingredients, i.e., tegafur, gimeracil, and oteracil potassium. Preferably, the pharmaceutical agent is administered concurrently with, or within four hours before or after the administration of the antitumor agent containing the three active ingredients, i.e., tegafur, gimeracil, and oteracil potassium, and more preferably within two hours of the administration of the antitumor preparation.

Unit dosage forms for administering the pharmaceutical agent containing, as an active ingredient, at least one ingredient selected from the group consisting of folinic acid and pharmacologically acceptable salts thereof, for the treatment of malignant tumors in mammals, including humans, are not particularly limited, and can be suitably selected according to the purpose of the treatment. Specific examples of such unit dosage forms include parenteral forms such as injections, suppositories, ophthalmic solutions, ointments, aerosols, and the like; and oral forms such as tablets, coated tablets, powders, granules, capsules, fluids, pills, suspensions, emulsions, and the like, with oral forms being preferred. These dosage forms can be produced according to methods generally known in the art.

The pharmaceutical agent containing l-OHP as an active ingredient is prepared into a pharmaceutical composition according to a general method, using suitable pharmaceutical carriers. Examples of usable carriers include those generally used for drugs, such as excipients, binders, disintegrators, lubricants, colorants, taste enhancers, flavor enhancers, and surfactants. The pharmaceutical agent that has been prepared into a desired unit dosage form can be administered concurrently with, or separately from, the antitumor agent containing the three active ingredients, i.e., tegafur, gimeracil, and oteracil potassium, that has also been prepared into a desired unit dosage form. More specifically, the pharmaceutical agent of the invention containing l-OHP as an active ingredient can be administered at any time point, i.e., before, after, or concurrently with, the administration of the antitumor agent containing the three active ingredients, i.e., tegafur, gimeracil, and oteracil potassium. Preferably, the pharmaceutical agent is administered concurrently with, or within four hours before or after the administration of the antitumor agent containing the three active ingredients, i.e., tegafur, gimeracil, and oteracil potassium, and more preferably within two hours of the administration of the antitumor preparation.

Unit dosage forms for administering the pharmaceutical agent of the invention containing l-OHP as an active ingredient, for the treatment of malignant tumors in mammals, including humans, are not particularly limited, and can be suitably selected according to the purpose of the treatment. Specific examples of such unit dosage forms include parenteral forms such as injections, suppositories, ophthalmic solutions, ointments, aerosols, and the like; and oral forms such as tablets, coated tablets, powders, granules, capsules, fluids, pills, suspensions, emulsions, and the like, with injections being preferred. Preferably, the pharmaceutical agent containing l-OHP is administered by intravenous, intramuscular, or subcutaneous injection. These dosage forms can be produced according to methods generally known in the art.

The antitumor preparation of the invention may also be an antitumor preparation that contains, in addition to the antitumor agent containing the three active ingredients, i.e., tegafur, gimeracil, and oteracil potassium, the above-mentioned active ingredients, i.e., l-OHP and at least one ingredient selected from the group consisting of folinic acid and pharmacologically acceptable salts thereof. This antitumor preparation is in a pharmaceutical form that comprises a plurality of pharmaceutical agents, each containing one or a desired combination of the antitumor agent containing the three active ingredients, i.e., tegafur, gimeracil, and oteracil potassium, at least one ingredient selected from the group consisting of folinic acid and pharmacologically acceptable salts thereof, and l-OHP; or in a pharmaceutical form that comprises a single pharmaceutical agent containing all of the active ingredients. That is to say, the antitumor preparation of the invention may be a one-part drug that contains all of the above ingredients, or a multi-part drug that comprises a pharmaceutical agent that contains one or two ingredients and a pharmaceutical agent that contains other ingredient(s). Particularly preferred is a three-part drug that separately comprises a combination drug containing the three active ingredients, i.e., tegafur, gimeracil, and oteracil potassium; a pharmaceutical agent containing, as an active ingredient, at least one ingredient selected from the group consisting of folinic acid and pharmacologically acceptable salts thereof; and a pharmaceutical agent containing l-OHP as an active ingredient.

Also preferred is a two-part drug that comprises a combination drug containing, as active ingredients, the three ingredients, i.e., tegafur, gimeracil, and oteracil potassium, and at least one ingredient selected from the group consisting of folinic acid and pharmacologically acceptable salts thereof; and a pharmaceutical agent containing l-OHP as an active ingredient. In this case, the combination drug may be in a pharmaceutical form that comprises a plurality of pharmaceutical agents, each containing one or a desired combination of the various active ingredients, instead of being in a pharmaceutical form that comprises a single pharmaceutical agent containing all of the active ingredients.

The proportion of each ingredient in the antitumor preparation is not particularly limited, regardless of whether the antitumor preparation is a one-part drug or multi-part drug; typically, however, per mole of tegafur, the proportion of gimeracil is from about 0.1 to about 5 mol, and preferably about 0.1 to about 1.5 mol; the proportion of oteracil potassium is from about 0.1 to about 5 mol, and preferably about 0.2 to about 2 mol; the proportion of the at least one ingredient selected from the group consisting of folinic acid and pharmacologically acceptable salts thereof is from about 0.01 to about 10 mol, preferably about 0.05 to about 5 mol, and more preferably about 0.1 to about 2 mol; and the proportion of l-OHP is from about 0.1 to about 5 mol, preferably about 0.3 to about 3 mol, and more preferably about 0.4 to about 2 mol.

In particular, the molar ratio of tegafur, gimeracil, oteracil potassium, at least one ingredient selected from the group consisting of folinic acid and pharmacologically acceptable salts thereof, and l-OHP is about 1:0.4:1:0.01 to 10:0.1 to 5, more preferably about 1:0.4:1:0.05 to 5:0.3 to 3, and still more preferably about 1:0.4:1:0.1 to 2:0.4 to 2. In the case of a three-part drug, which is a preferred embodiment, that separately comprises a combination drug containing the three active ingredients, i.e., tegafur, gimeracil, and oteracil potassium, a pharmaceutical agent containing, as an active ingredient, at least one ingredient selected from the group consisting of folinic acid and pharmacologically acceptable salts thereof, and a pharmaceutical agent containing l-OHP as an active ingredient; the molar ratio of tegafur/gimeracil/oteracil potassium in the combination drug is 1:0.4:1; the proportion of the pharmaceutical agent containing, as an active ingredient, at least one ingredient selected from the group consisting of folinic acid and pharmacologically acceptable salts thereof is about 0.01 to about 10 mol, preferably about 0.05 to about 5 mol, and more preferably about 0.1 to about 2, per mole of tegafur; and the proportion of the pharmaceutical agent containing l-OHP is about 0.1 to about 5 mol, preferably about 0.3 to about 3 mol, and more preferably about 0.4 to about 2 mol, per mole of tegafur.

Furthermore, in the invention, the combination drug containing tegafur, gimeracil, and oteracil potassium, the pharmaceutical agent containing, as an active ingredient, at least one ingredient selected from the group consisting of folinic acid and pharmacologically acceptable salts thereof, and the pharmaceutical agent containing l-OHP may be packaged in a kit comprising a combination of pharmaceutical compositions for treating cancer in a mammal.

The kit comprises:

(a) an antitumor composition containing tegafur in a therapeutically effective amount, gimeracil in an amount effective for enhancing antitumor effects, and oteracil potassium in an amount effective for reducing side effects;

(b) a composition containing at least one ingredient selected from the group consisting of folinic acid and pharmacologically acceptable salts thereof in an amount effective for enhancing antitumor effects; and (c) a composition containing l-OHP in an amount effective for enhancing antitumor effects.

The compositions that constitute the kit may be in various known pharmaceutical forms, and are typically contained in various types of generally used containers according to their pharmaceutical forms.

As used herein, the phrase "kit comprising a combination of pharmaceutical compositions for treating cancer" means a kit comprising a desired combination of the above-mentioned pharmaceutical compositions, or a kit comprising all of the active ingredients in a single form.

The kit may be a kit for treating cancer in a mammal, comprising, for example, at least the above-mentioned three compositions (a) to (c), and at least two containers for these compositions, wherein the compositions (a) and (c) are contained in different containers. The compositions (a) to (c) are preferably in a pharmaceutical form combined with pharmacologically acceptable carrier(s). Provided that the kit comprises the compositions (a) and (c) in different containers, the composition (b) may be contained in a container different from the other two compositions; or composition (b) may be mixed with the composition (a) or (c) and contained in the same container as that of the composition (a) or (c).

Unit dosage forms for administering the antitumor preparation of the present invention, for the treatment of malignant tumors in mammals, including humans suffering malignant tumors, are not particularly limited, and can be selected according to the purpose of the treatment. Specific examples of such unit dosage forms include parenteral forms such as injections, suppositories, ophthalmic solutions, ointments, aerosols, and the like; and oral forms such as tablets, coated tablets, powders, granules, capsules, fluids, pills, suspensions, emulsions, and the like. These dosage forms can be produced according to methods generally known in the art.

When the antitumor preparation of the invention is prepared in the form of solid oral preparations, such as tablets, powders, pellets, and the like, examples of usable carriers include the following: excipients such as lactose, saccharose, sodium chloride, glucose, urea, starch, calcium carbonate, kaolin, crystalline cellulose, silicic acid, methylcellulose, glycerol, sodium alginate, gum arabic, and the like; binders such as simple syrups, liquid glucose, liquid starch, gelatin solutions, polyvinyl alcohol, polyvinyl ether, polyvinylpyrrolidone, carboxymethylcellulose, shellac, methylcellulose, ethylcellulose, water, ethanol, potassium phosphate, and the like; disintegrators such as dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, lactose, and the like; disintegration inhibitors such as saccharose, stearic acid, cocoa butter, hydrogenated oils, and the like; absorption enhancers such as sodium lauryl sulfate and the like; humectants such as glycerol, starch, and the like; adsorbents such as starch, lactose, kaolin, bentonite, colloidal silicic acid, and the like; lubricants such as purified talc, stearic acid salts, powdered boric acid, polyethylene glycol, and the like; etc. Tablets may be optionally provided with general coatings to provide sugar-coated tablets, gelatin-coated tablets, enteric-coated tablets, film-coated tablets, double-layer tablets, multi-layer tablets, and the like.

In the preparation of pills, usable carriers include excipients such as glucose, lactose, starch, cacao butter, hydrogenated vegetable oils, kaolin, talc, and the like; binders such as powdered gum arabic, powdered tragacanth, gelatin, and the like; disintegrants such as laminaran, agar, and the like; etc.

Capsules are prepared by mixing the active ingredients with the above-mentioned various carriers, and by filling hard gelatin capsules, soft capsules, or the like with the mixture.

In the preparation of suppositories, usable carriers include polyethylene glycol, cacao butter, lanolin, higher alcohols, esters of higher alcohols, gelatin, semi-synthetic glycerides, Witepsol (registered trademark, Dynamite Nobel Inc.), etc.

In the preparation of injections, usable carriers include diluents such as water, ethyl alcohol, macrogol, propylene glycol, ethoxylated isostearyl alcohol, polyoxylated isostearyl alcohol, polyoxyethylene sorbitan fatty acid esters, and the like; pH-adjusters such as sodium citrate, sodium acetate, sodium phosphate, and the like; buffers such as dipotassium phosphate, trisodium phosphate, sodium hydrogen phosphate, sodium citrate, and the like; stabilizers such as sodium pyrosulfite, EDTA, thioglycolic acid, thiolactic acid, and the like; saccharides such as mannitol, inositol, maltose, sucrose, lactose, and the like for use as binders in freeze-drying; etc. In this case, glucose or glycerol may be incorporated in the pharmaceutical agent in an amount sufficient to prepare an isotonic solution. General auxiliary solvents, soothing agents, topical anesthetics, and the like may also be added to the solution. Subcutaneous, intramuscular, and intravenous injections can be prepared according to common methods by adding the above-mentioned carriers.

Liquid preparations may take the forms of water-based or oil-based suspensions, solutions, syrups, or elixirs, and can be prepared according to common methods, using generally used additives.

When the pharmaceutical agent is prepared in the form of ointments, e.g., pastes, creams, and gels, usable diluents include white petrolatum, paraffin, glycerol, cellulose derivatives, polyethylene glycol, silicon, bentonite, etc.

In the antitumor preparation of the invention, the amount of each of the active ingredients, which are tegafur, gimeracil, and oteracil potassium, the at least one ingredient selected from the group consisting of folinic acid and pharmacologically acceptable salts thereof, and l-OHP, may vary according to the dosage form, route of administration, dosing schedule, and the like. Thus, the amount of each active ingredient is not particularly limited, and may be suitably selected. Typically, the amount of the active ingredient in each pharmaceutical agent may be about 1 to about 70 wt %.

The mode of administration of the pharmaceutical agent of the invention is not particularly limited, and can be determined according to the pharmaceutical form, the patient's age, sex, and other conditions, the severity of the patient's symptoms, and the like. Usable modes of administration include enteral, oral, rectal, intraoral, intraarterial, intravenous, and transdermal administration. For example, tablets, pills, solutions, suspensions, emulsions, granules, capsules, and the like are administered orally; injections are administered intraarterially or intravenously; suppositories are administered intrarectally; and ointments are applied to the skin, the mucous membranes in the mouth, and the like. For example, in the pharmaceutical agent of the invention, the combination drug containing tegafur, gimeracil, and oteracil potassium, and the pharmaceutical agent containing, as an active ingredient, at least one ingredient selected from the group consisting of folinic acid and pharmacologically acceptable salts thereof can be orally administered; and the pharmaceutical agent containing l-OHP as an active ingredient can be intravenously administered.

The dose of each of the active ingredients in the invention can be suitably selected according to the use, the patient's age, sex, the severity of the patient's symptoms, other conditions, and the like. The antitumor-effect potentiator and the antitumor preparation of the invention can be administered in divided doses, i.e., about one to four doses, per day.

In the case of oral administration, tegafur may be administered at a dose of about 0.1 to 100 mg/kg/day, preferably about 0.2 to 40 mg/kg/day, and more preferably about 0.5 to 20 mg/kg/day; gimeracil may be administered at a dose of about 0.02 to 30 mg/kg/day, preferably about 0.05 to 12 mg/kg/day, and more preferably about 0.1 to 6 mg/kg/day; oteracil potassium may be administered at a dose of about 0.1 to 100 mg/kg/day, preferably about 0.2 to 40 mg/kg/day, and more preferably about 0.5 to 20 mg/kg/day; the at least one ingredient selected from the group consisting of folinic acid and pharmacologically acceptable salts thereof may be administered at a dose of about 0.05 to 1000 mg/kg/day, preferably about 0.1 to 100 mg/kg/day, and more preferably about 0.2 to 10 mg/kg/day, calculated as the amount of folinic acid; and l-OHP may be administered at a dose of about 0.08 to 200 mg/kg/day, preferably about 0.15 to 80 mg/kg/day, and more preferably about 0.4 to 40 mg/kg/day.

In the case of an injection, typically, the daily dose of the combination drug for an adult may be about 0.1 to about 100 mg/kg when calculated as the amount of tegafur; the daily dose, for an adult, of the at least one ingredient selected from the group consisting of folinic acid and pharmacologically acceptable salts thereof may be about 0.05 to about 1000 mg/kg when calculated as the amount of folinic acid; and the daily dose of l-OHP for an adult may be about 0.08 to about 200 mg/kg. The injection may be diluted as needed with a saline solution or 5% aqueous glucose solution, and gradually administered over a period of 5 minutes or longer.

In the case of a suppository, typically, the daily dose of the combination drug for an adult may be about 0.1 to about 100 mg/kg when calculated as the amount of tegafur; the daily dose, for an adult, of the at least one ingredient selected from the group consisting of folinic acid and pharmacologically acceptable salts thereof may be about 0.05 to about 1000 mg/kg when calculated as the amount of folinic acid; and the daily dose of l-OHP for an adult may be about 0.08 to about 200 mg/kg. The suppository may be administered once or twice a day at an interval of 6 to 12 hours by inserting it into the rectum.

For example, l-OHP may be administered by intravenous drip infusion at a dose of 85 mg/m$^2$ on day one; and the combination drug of tegafur/gimeracil/oteracil potassium and the at least one ingredient selected from the group consisting of folinic acid and pharmacologically acceptable salts thereof may be orally administered at a dose of 40 mg/m$^2$/bid (calculated as the amount of tegafur) and a dose of 25 mg/body/bid, respectively, from day one for one week.

The types of malignant tumors that can be treated by administering the pharmaceutical agent of the invention are not limited, insofar as the active principle, i.e., 5-FU, is reactive thereto. Examples of such malignant tumors include head and neck cancer, stomach cancer, colon cancer, rectal cancer, liver cancer, gallbladder/biliary cancer, pancreatic cancer, lung cancer, breast cancer, vesical cancer, prostatic cancer, uterine cancer, pharyngeal cancer, esophageal cancer, renal cancer, ovarian cancer, etc. In particular, the pharmaceutical agent of the invention can be expected to be highly effective against colon cancer, rectal cancer, breast cancer, esophageal cancer, stomach cancer, head and neck cancer, lung cancer, pancreatic cancer, and gallbladder/biliary cancer. Moreover, the pharmaceutical agent can be expected to be highly effective against typical drug-resistant tumors and tumors that are beginning to become drug-resistant.

Advantageous Effects of Invention

The antitumor preparation, kit, method for treating cancer, and the like of the invention can provide antitumor effects superior to those of the three-drug combination of tegafur, gimeracil, and oteracil potassium, which is a known antitumor preparation, or the pharmaceutical agent containing l-OHP alone, without increasing toxicity (in particular, gastrointestinal and bone marrow toxicities). Moreover, the antitumor effects attained by the invention are superior to those obtained by standard therapies for the treatment of colon cancer. Furthermore, the antitumor preparation, kit, method for treating cancer, and the like of the invention are expected to provide excellent antitumor-effect potentiation and antitumor effects against 5-FU-resistant tumors or multi-drug resistant tumors.

DESCRIPTION OF EMBODIMENTS

The present invention will be described in greater detail below with reference to Examples; however, the invention is not limited to these Examples.

Examples

Chemotherapeutically untreated patients (humans) with advanced and/or recurrent colorectal cancers were orally administered with 40 mg/m$^2$ of TS-1 (calculated as the amount of tegafur) and 25 mg/body of calcium folinate concurrently twice a day, after breakfast and dinner, for one week, followed by a rest period of one week; on day 1 of administration, 85 mg/m$^2$ of l-OHP was administered concurrently with TS-1 by intravenous drip infusion over a period of 2 hours. Taking this schedule as one cycle, clinical trials were conducted on six subjects (male: 4, female: 2) by repeating this cycle.

As a result, the antitumor effects were such that the six subjects reached a partial response (PR), with the response rate being extremely high, i.e., 100%. The time to treatment failure (TTF) was 194 days, and the progression-free survival (PFS) was 238 days; even after about one and a half years from the start of the treatment, five out of six subjects have survived, and overall survival has not been reached yet. It has been reported that the combination therapy of TS-1 and l-OHP resulted in a response rate of 50% and a progression-free survival of 196 days (6.4 months), and that the combination therapy of TS-1 and calcium folinate resulted in a response rate of 57% and a progression-free survival of 6.7 months. Therefore, the combination therapy of this Example achieved results superior to any of these combination therapies (British Journal of Cancer, Vol. 98, 1034-1038, 2008, ASCO Annual Meeting 2007).

TTF, PFS, and overall survival are endpoints that are standardly used in clinical trials in the area of tumors, and have the same definitions as standardly used.

TTF is defined herein as the period of time measured from the initial date of administration until the earliest date of the following: the date that progressive disease (PD) was diagnosed; the date of cessation of the clinical trial; or the date of death of the patient if the patient died before the date of cessation of the clinical trial.

PFS is defined as the period of time measured from the date of registration until PD was diagnosed. If the patient died before the symptoms were diagnosed as PD, the date of death is determined to be the date that PD was diagnosed.

In any of the above cases, if other cancer treatment (such as anticancer drug treatment and radiation therapy) was performed for reasons other than PD, the date that the treatment was performed is used. If radical surgery was performed, the date of recurrence is used.

Overall survival is defined as the period of time measured from the date of registration until the date of death.

Within the initial two cycles, i.e., the period of evaluating dose-limiting toxicity, side effects were observed only in one subject who showed diarrhea and hypertension of grade 3. Throughout the total treatment cycles, the major side effects were only diarrhea (two subjects), anorexia (two subjects), nausea (one subject), peripheral neuropathy (one subject), hypertension (one subject), and amylase elevation (one subject) of grade 3 or 4. Therefore, the side effects were within an acceptable level.

Presently, the average number of treatment cycles has reached 12 (range: 6-34), revealing that repeated administration can be further continued, and that this trial can be conducted without problems, even in view of the side effects.

The test results shown above have revealed that the combination therapy of the combination drug of tegafur/gimeracil/oteracil potassium, calcium folinate, and l-OHP significantly increases the antitumor activity, as compared to the sole use of the combination drug of tegafur/gimeracil/oteracil potassium or standard chemotherapies for colon cancer, without significantly increasing the side effects. Therefore, the combination therapy of the invention has proved to be extremely effective.

The invention claimed is:

1. A method for treating cancer comprising co-administering to a mammal (1) a combination drug of tegafur/gimeracil/oteracil potassium in a therapeutically effective amount, (2) at least one ingredient selected from the group consisting of folinic acid and pharmacologically acceptable salts thereof in an amount effective for enhancing antitumor effects, and (3) cis-oxalate(1R,2R-diaminocyclohexane)platinum(II) in an amount effective for enhancing antitumor effects.

2. The method for treating cancer according to claim 1, wherein the combination drug of tegafur/gimeracil/oteracil potassium comprises tegafur, gimeracil, and oteracil potassium in a molar ratio of 1:0.4:1.

3. The method for treating cancer according to claim 1, wherein the proportions of the active ingredients are such that, per mole of tegafur, the proportion of gimeracil is 0.1 to 5 mol; the proportion of oteracil potassium is 0.1 to 5 mol; the proportion of the at least one ingredient selected from the group consisting of folinic acid and pharmacologically acceptable salts thereof is 0.01 to 10 mol; and the proportion of cis-oxalate(1R,2R-diaminocyclohexane)platinum(II) is 0.1 to 5 mol.

4. The method for treating cancer according to claim 3, wherein the molar ratio of the active ingredients is such that tegafur/gimeracil/oteracil potassium/the at least one ingredient selected from the group consisting of folinic acid and pharmacologically acceptable salts thereof/cis-oxalate(1R,2R-diaminocyclohexane)platinum(II)=1:0.4:1:0.01 to 10:0.1 to 5.

5. The method for treating cancer according to claim 1, wherein the combination drug of tegafur/gimeracil/oteracil potassium and a pharmaceutical agent containing, as an active ingredient, at least one ingredient selected from the group consisting of folinic acid and pharmacologically acceptable salts thereof are orally administered; and a pharmaceutical agent containing cis-oxalate(1R,2R-diaminocyclohexane)platinum(II) as an active ingredient is administered intravenously, intramuscularly, or subcutaneously.

6. The method for treating cancer according to claim 1, wherein the dose of tegafur of the combination drug of tegafur/gimeracil/oteracil potassium is 40 mg/m$^2$/bid; the dose of the at least one ingredient selected from the group consisting of folinic acid and pharmacologically acceptable salts thereof is 25 mg/body/bid; and the dose of cis-oxalate(1R,2R-diaminocyclohexane)platinum(II) is 85 mg/m$^2$.

7. The method for treating cancer according to claim 1, wherein cis-oxalate(1R,2R-diaminocyclohexane)platinum(II) is administered by intraveneous drip infusion, and the combination drug of tegafur/gimeracil/oteracil potassium and the at least one ingredient selected from the group consisting of folinic acid and pharmacologically acceptable salts thereof are orally administered; and wherein the cis-oxalate(1R,2R-diaminocyclohexane)platinum(II) is administered at a dose of 85 mg/m$^2$ on day one, and the combination drug of tegafur/gimeracil/oteracil potassium and the at least one ingredient selected from the group consisting of folinic acid and pharmacologically acceptable salts thereof are administered at doses of 40 mg/m$^2$/bid (calculated as the amount of tegafur) and 25 mg/body/bid, respectively, from day one for one week.

* * * * *